United States Patent
Lu et al.

(10) Patent No.: US 9,758,415 B2
(45) Date of Patent: Sep. 12, 2017

(54) MICROORGANISMS-IMMOBILIZED FELT-BASED RESIN FOR THE TREATMENT OF PHENOLIC EFFLUENTS AND A PREPARATION METHOD THEREOF

(71) Applicant: SOOCHOW UNIVERSITY, Suzhou (CN)

(72) Inventors: Jianmei Lu, Suzhou (CN); Najun Li, Suzhou (CN)

(73) Assignee: Soochow University, Suzhou (CN)

( * ) Notice: Subject to any disclaimer, the term of this patent is extended or adjusted under 35 U.S.C. 154(b) by 358 days.

(21) Appl. No.: 14/025,353

(22) Filed: Sep. 12, 2013

(65) Prior Publication Data

US 2014/0102979 A1    Apr. 17, 2014

(30) Foreign Application Priority Data

Oct. 15, 2012 (CN) .......................... 2012 1 0389741

(51) Int. Cl.
| | |
|---|---|
| C02F 3/00 | (2006.01) |
| C12N 11/14 | (2006.01) |
| C12N 11/02 | (2006.01) |
| C12N 11/08 | (2006.01) |
| C12N 11/06 | (2006.01) |
| C02F 3/34 | (2006.01) |
| C02F 3/10 | (2006.01) |
| C02F 101/34 | (2006.01) |
| C02F 103/28 | (2006.01) |
| C02F 103/36 | (2006.01) |
| C02F 103/38 | (2006.01) |

(52) U.S. Cl.
CPC .............. *C02F 3/348* (2013.01); *C02F 3/108* (2013.01); *C12N 11/08* (2013.01); *C02F 3/103* (2013.01); *C02F 3/341* (2013.01); *C02F 2101/345* (2013.01); *C02F 2103/28* (2013.01); *C02F 2103/365* (2013.01); *C02F 2103/38* (2013.01); *Y02W 10/15* (2015.05)

(58) Field of Classification Search
CPC .......... C02F 3/108; C02F 3/103; C12N 11/04; C12N 11/00; C12N 11/02; C12N 11/08; C08F 220/56
USPC ......... 435/180, 176, 177, 182, 174; 210/615
See application file for complete search history.

(56) References Cited

U.S. PATENT DOCUMENTS 4,981,798 A * 1/1991 Kamakura ............. C12N 11/12
                                                    435/177
5,185,415 A * 2/1993 Kawabata ............. A01N 25/10
                                                    210/616

(Continued)

OTHER PUBLICATIONS

Chen et al, Biodegradation of phenol by PAA-Immobilized candida tropicalis, Enzyme and Microbial Technology 31, 2002, pp. 490-497.*

(Continued)

*Primary Examiner* — Claire Norris
(74) *Attorney, Agent, or Firm* — SZDC Law P.C.

(57) ABSTRACT

A method of preparing a microorganisms-immobilized felt-based resin includes the following steps: providing a mixture of an acrylate monomer, an initiator, a solvent, and water; adding a felt to the mixture; initiating a polymerization reaction of the mixture to form a felt-based resin; and immobilizing microorganisms on the felt-based resin to form the microorganisms-immobilized felt-based resin.

11 Claims, 6 Drawing Sheets

Optical and microscopic photographs for matrix and immobilized bacterial cells

(56) References Cited

U.S. PATENT DOCUMENTS

| | | | | |
|---|---|---|---|---|
| 5,405,618 A * | 4/1995 | Buttery | ............... | C08F 2/44 |
| | | | | 424/486 |
| 5,580,770 A * | 12/1996 | DeFilippi | ............... | C02F 3/06 |
| | | | | 210/615 |
| 2007/0078243 A1 * | 4/2007 | Moore | ............... | C08F 220/38 |
| | | | | 526/258 |
| 2010/0264097 A1 * | 10/2010 | Sun | ............... | A61K 9/0092 |
| | | | | 210/767 |
| 2012/0064024 A1 * | 3/2012 | Nguyen | ............... | A61K 8/8182 |
| | | | | 424/70.15 |

OTHER PUBLICATIONS

El-Naas et al, Biodegradation of phenol by Pseudomonas putida immobilized in polyvinyl alcohon (PVA) gel, Journal of Hazardous Materials 164, 2009, pp. 720-725.*

* cited by examiner

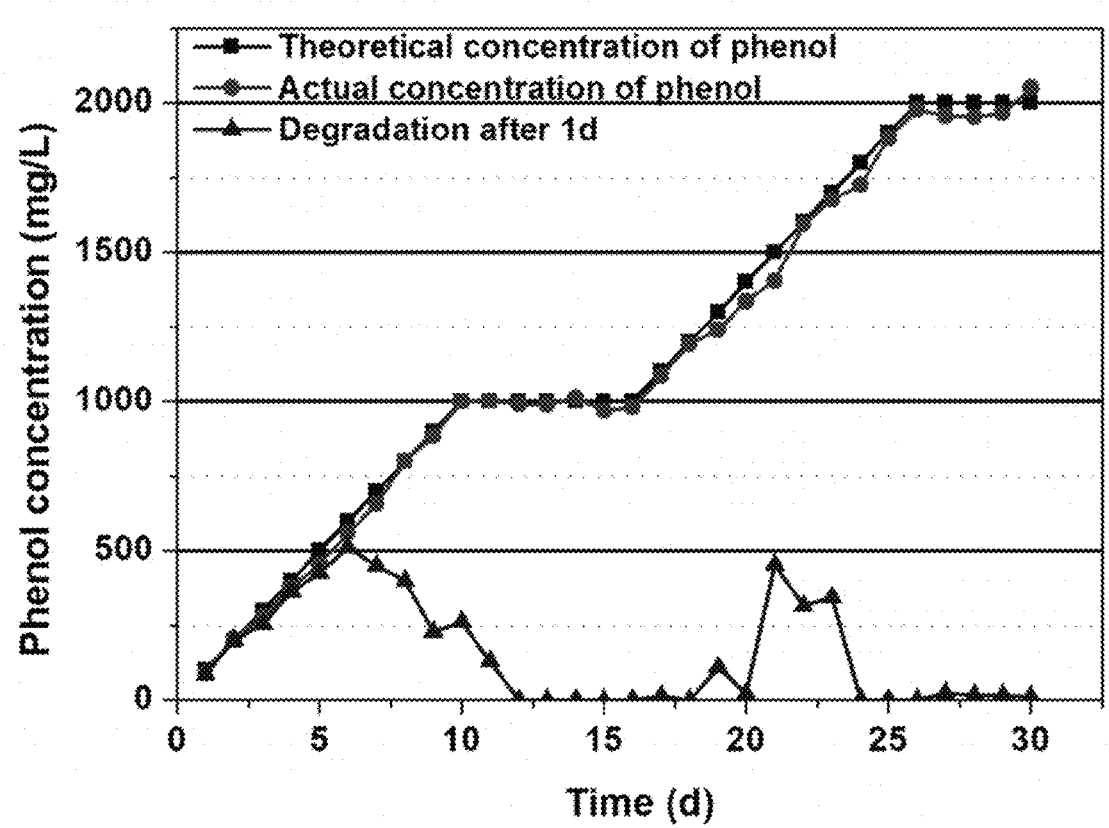
Fig. 1 Acclimatization process of *Pseudomonas putida*

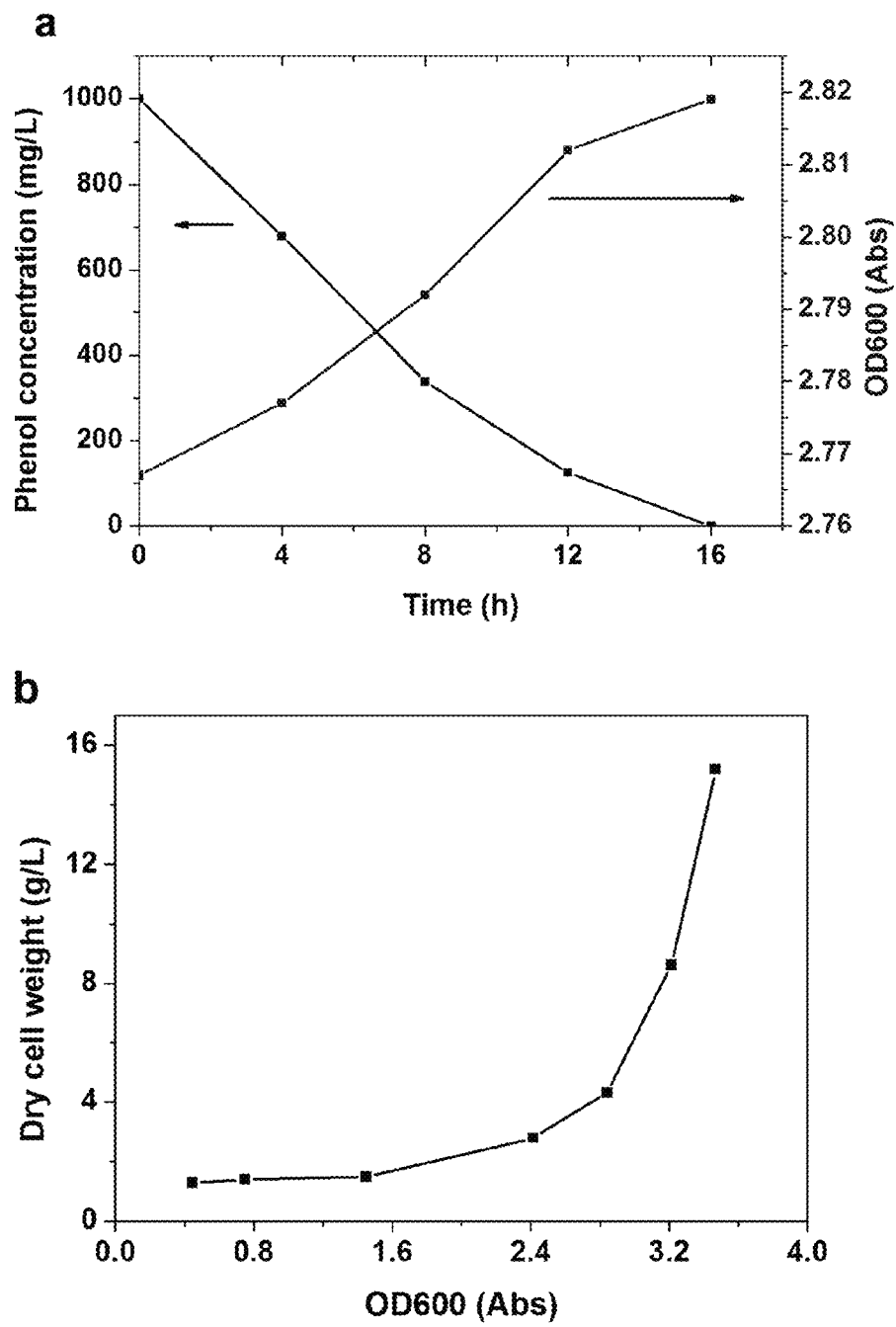
Fig. 2 (a) Biodegradation curve and $OD_{600}$ of free *Pseudomonas putida* and (b) the relatively conversion curve of DCW and $OD_{600}$

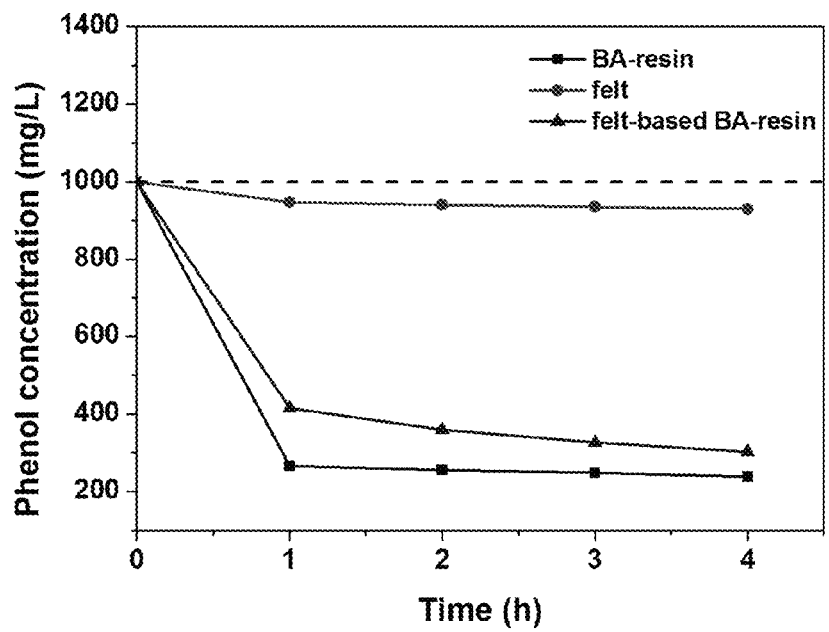
Fig. 3 The adsorption of phenol by felt-based BA-resin in comparison with its component materials
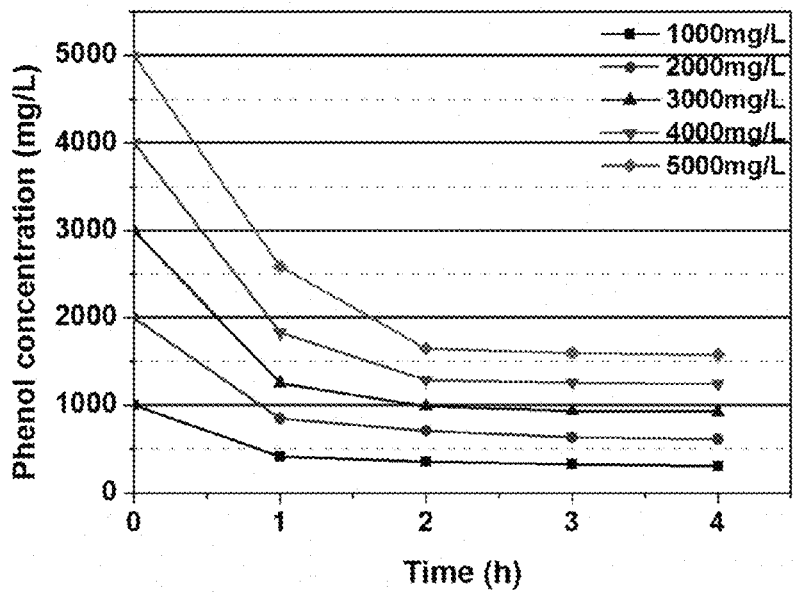
Fig. 4 Equilibrium adsorption of phenol by felt-based BA-resin at different initial concentrations

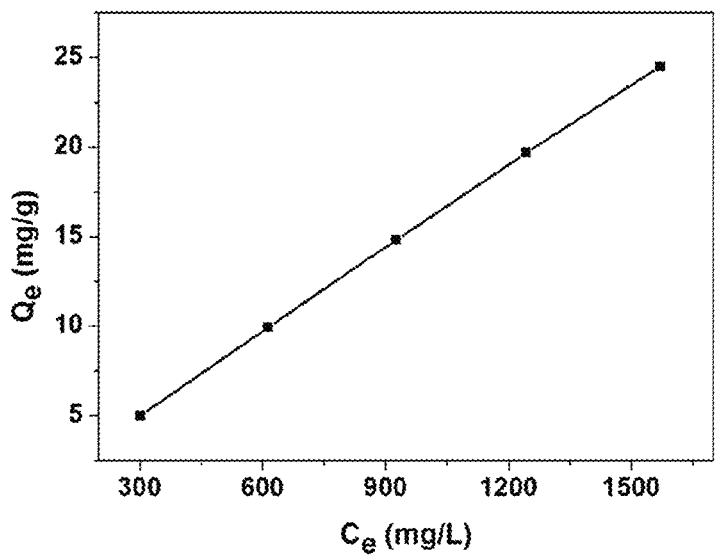
Fig. 5 Adsorption isotherm of phenol by felt-based BA-resin
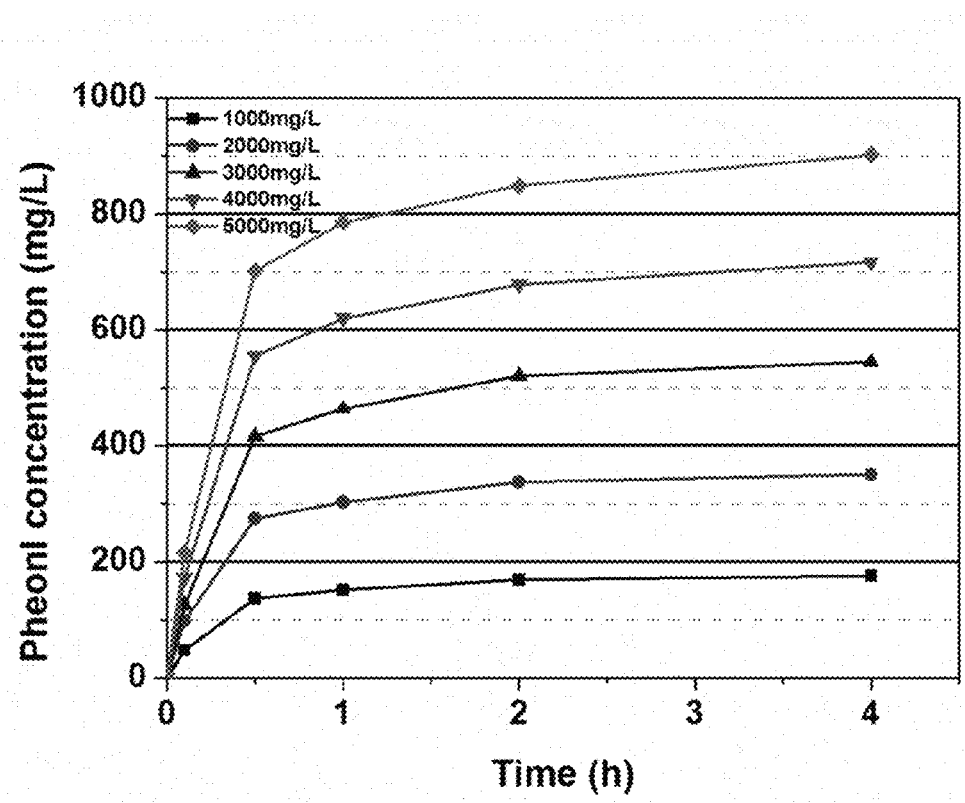
Fig. 6 Slow-release curves of phenol from the felt-based BA-Resins

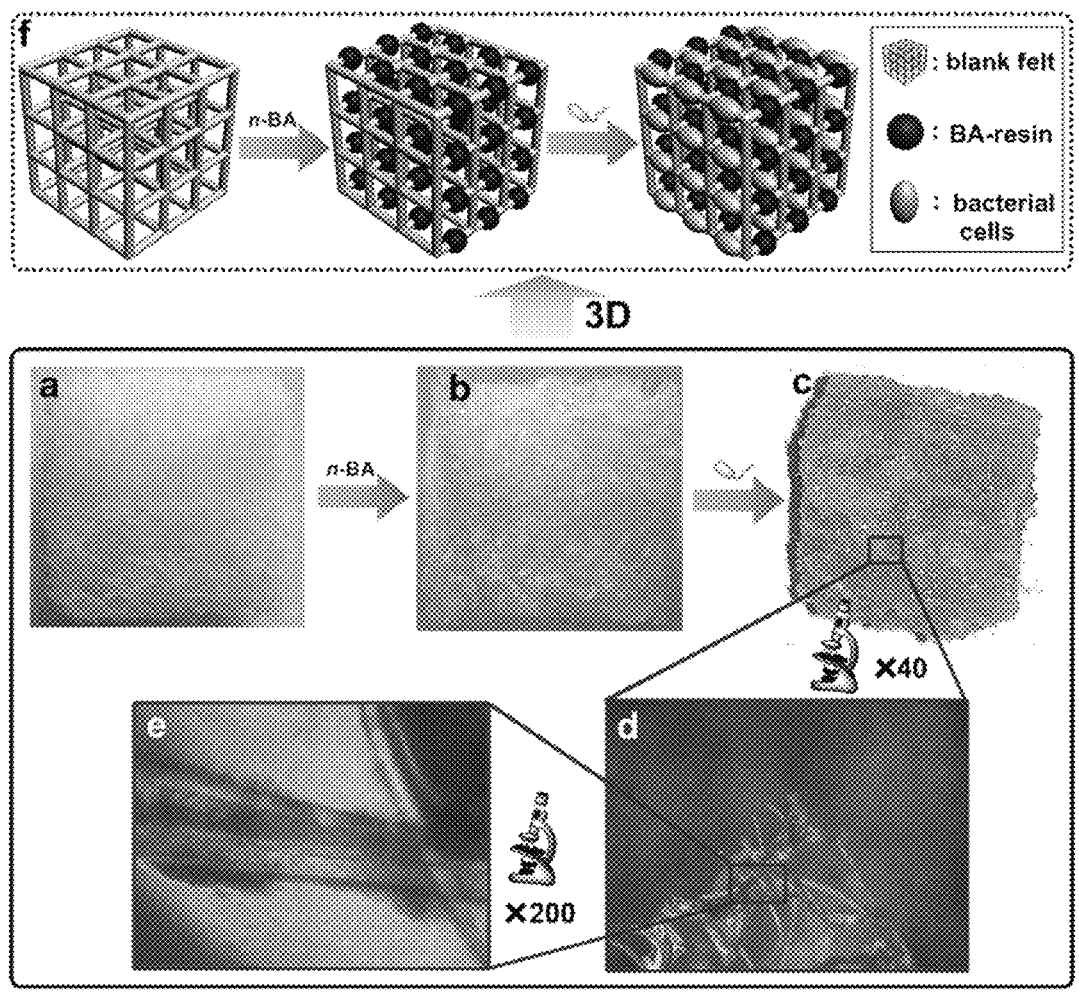
Fig. 7 Optical and microscopic photographs for matrix and immobilized bacterial cells

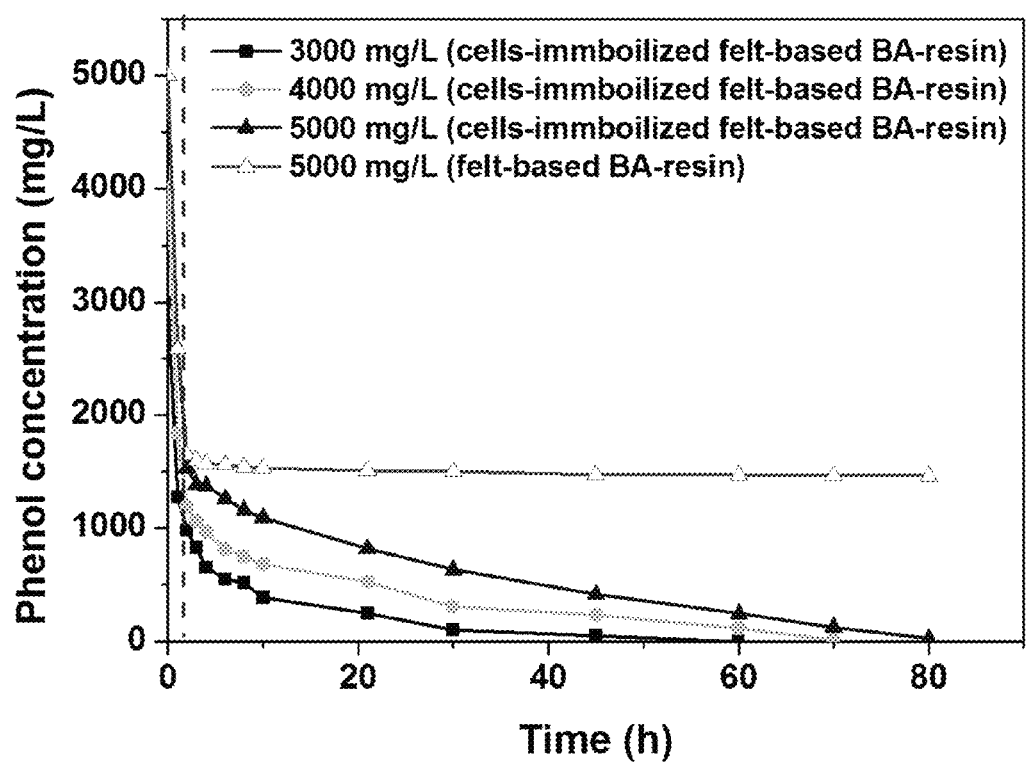
Fig. 8 The adsorption-biodegradation process of cells-immobilized felt-based BA-resin

MICROORGANISMS-IMMOBILIZED FELT-BASED RESIN FOR THE TREATMENT OF PHENOLIC EFFLUENTS AND A PREPARATION METHOD THEREOF

The present invention claims priority to Chinese Patent Application No. 201210389741.4, filed on Oct. 15, 2012.

BACKGROUND OF THE INVENTION

Field of the Invention

The present invention relates to microorganisms-immobilized felt-based resin for the treatment of phenolic effluents and a preparation method of the microorganisms-immobilized felt-based resin.

Discussion of the Related Art

Phenolic compounds, easily found in oil refineries, chemical, dye, paper making and many petrochemical industries, lead to environmental pollution. Phenolic compounds limit the growth of aquatic life and harm people's health even at a low concentration. Therefore, phenolic compounds have been listed as priority pollutants by the United States Environmental Protection Agency and other countries.

Various technical processes, such as solvent extraction, biodegradation, adsorption, and chemical oxidation, have been attempted to remove phenolic compounds from wastewater. But lots of disadvantages limit their applications in the removal of phenolic compounds. For example, adsorption is an effective and commonly used techniques in either laboratory or industrial scale, but this physicochemical method has been proved to be costly and a secondary pollution would be caused by the containments-containing adsorbents. Microbial degradation method has been attracted increasing attention for the treatment of wastewaters, especially with the development of immobilization technologies for microorganisms. However, the microorganisms can only used to treat phenol-containing effluent at low concentrations (100-1000 mg/L). Therefore, a pre-treatment is needed for the phenolic waste water from industrial production processes, in which the phenol concentration often reaches 3000-5000 mg/L.

There is a need for a practical, economical and environmentally-friendly technique that can be used to treat phenol-containing effluent at high concentrations (3000-5000 mg/L).

SUMMARY OF THE INVENTION

An objective of the present invention is to provide a method of preparing a microorganisms-immobilized felt-based resin. The method includes providing a mixture of an acrylate monomer, an initiator, an organic solvent, and water, adding a felt to the mixture, initiating a polymerization reaction of the mixture to form a felt-based resin, and immobilizing microorganisms on the felt-based resin to form the microorganisms-immobilized felt-based resin.

The microorganisms can be *Pseudomonas putida, Candida albicans, Rhodococcus*, or *Trichosporon*. The acrylate monomer can be methyl acrylate, ethyl acrylate, propyl acrylate, isopropyl acrylate, n-butyl acrylate, isobutyl acrylate, n-amyl acrylate, isoamyl acrylate, n-ethyl hexyl acrylate, 2-ethyl hexyl acrylate, 2-hydroxy ethyl acrylate, methyl methacrylate, ethyl methacrylate, propyl methacrylate, isopropyl methacrylate, n-butyl methacrylate, isobutyl methacrylate, n-amyl methacrylate, isoamyl methacrylate, n-hexyl methacrylate, n-ethyl hexyl methacrylate, 2-ethyl hexyl methacrylate, hydroxyethyl methacrylate, or hydroxypropyl methacrylate. The initiator can be an organic peroxide initiator or an azo initiator. The organic solvent can be ethyl acetate, toluene, N-methyl-2-pyrollidinone, propylene carbonate, ethylene carbonate, butylene carbonate, dimethyl carbonate, diethyl carbonate, 1,2-dimethoxy ethane, 2-methyl tetrahydrofuran, dimethylsulfoxide, 1,3-dioxolane, formamide, dimethylformamide, dioxolane, acetonitrile, nitromethane, methyl formate, methyl acetate, phosphoric acid triester, trimethoxy methane, methyl sulfolane, 1,3-dimethyl-2-imidazolidinone, methyl propionate, or ethyl propionate.

The initiator can be in an amount of 0.01 wt % to 5 wt % based on the weight of the acrylate monomer, the organic solvent can be in an amount of 100 wt % to 200 wt % based on the weight of the acrylate monomer, and water can be in an amount of 100 wt % to 500 wt % based on the weight of the acrylate monomer. The felt can be polyester fiber, polypropylene fiber, acrylic fiber, polyacrylonitrile fiber, sponge, aramid fiber, or non-woven fabrics.

The microorganisms can be treated in an acclimatization process before immobilization. The acclimatization process includes gradually increasing a phenol concentration and gradually decreasing a glucose concentration. In one application, the phenol concentration increases from 0 to 2000 mg/L at a rate of 100 mg/L per day. In another application, the glucose concentration decreases from 1000 mg/L at a rate of 100 mg/L per day.

In one application, the felt includes fibers with a network structure and the microorganisms is evenly distributed on the surface and interspace of the fibers. In another application, the felt includes fibers with a network structure and the resin is evenly distributed on the surface and interspace of the fibers. In another application, the felt includes fibers with a network structure and the microorganisms and the resin are alternately distributed on the surface and interspace of the fibers.

Another objective of the present invention is to provide a microorganisms-immobilized felt-based resin prepared in accordance with the above-described method. The microorganisms-immobilized felt-based resin can treat a phenolic effluent having phenol concentration of 1000-5000 mg/L.

Another objective of the present invention is to provide a method of cleaning a phenolic effluent. The method includes preparing a microorganisms-immobilized felt-based resin prepared in accordance with the above-described method, and treating the phenolic effluent with the microorganisms-immobilized felt-based resin. The phenolic effluent can have a phenol concentration of 1000-5000 mg/L.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 1 shows an acclimatization process of *Pseudomonas putida* (initial phenol concentration=0 mg/L, initial glucose concentration=1000 mg/L, volum of MSM solution=50 mL, pH=7 and T=30° C.).

FIG. 2 shows (a) Biodegradation curve and $OD_{600}$ of free *Pseudomonas putida* (initial phenol concentration=1000 mg/L, volum of phenol solution=50 mL, pH=7 and T=30° C.) and (b) the relatively conversion curve of DCW and $OD_{600}$).

FIG. 3 shows the adsorption of phenol by felt-based BA-resin in comparison with its component materials (initial phenol concentration=1000 mg/L, volum of phenol solution=50 mL, pH=7 and T=303 K).

FIG. 4 shows the equilibrium adsorption of phenol by felt-based BA-resin at different initial concentrations (initial phenol concentration=1000, 2000, 3000, 4000, 5000 mg/L, weight of felt-based BA-resin=7.0 g, volume of phenol solution=50 mL, pH=7 and T=303 K).

FIG. 5 shows adsorption isotherm of phenol by felt-based BA-resin (initial phenol concentration=1000, 2000, 3000, 4000, 5000 mg/L, weight of felt-based BA-resin=7.0 g, volum of phenol solution=50 mL, pH=7 and T=303 K).

FIG. 6 shows slow-release curves of phenol from the felt-based BA-Resins in clean water after the saturated adsorption in phenol solution at different initial concentrations (initial phenol concentration=1000, 2000, 3000, 4000 and 5000 mg/L, replaced by distilled water, weight of felt-based BA-resin=7.0 g, volum of phenol solution=50 mL, pH=7 and T=303 K).

FIG. 7 shows optical and microscopic photographs for matrix and immobilized bacterial cells (a: blank felt, b: felt-based BA-resin, c: bacteria-immobilized felt-based BA-resin, d & e: 40 and 200-times magnified microscopic photographs of c).

FIG. 8 shows the adsorption-biodegradation process of cells-immobilized felt-based BA-resin at different initial phenol concentrations in comparison with cells-free felt-based BA-resin in the same conditions (initial phenol concentration=3000, 4000, 5000 mg/L, weight of resin=7.0 g, volum of phenol solution=50 mL, pH=7 and T=30° C.).

DETAILED DESCRIPTION OF THE ILLUSTRATED EMBODIMENTS

Reference will now be made in detail to embodiments of the present invention, examples of which are illustrated in the accompanying drawings.

The inventors reported that a felt-based resin can function as not only an adsorbent but also an immobilization matrix of the microorganisms for the removal of phenolic compounds at high concentration (1000-5000 mg/L) without any pre-treatment. Phenolic compounds used herein include phenols and compounds relating to, containing, or derived from phenols. Phenolic compounds are also referred as phenol or phenols herein.

The resin can be prepared by a polymerization of a monomer. The monomer can be an acrylate monomer, a vinyl monomer, or any suitable monomer that can be used to prepare a resin. Preferably, the monomer is an acrylate monomer. The acrylate monomer can be methyl acrylate, ethyl acrylate, propyl acrylate, isopropyl acrylate, n-butyl acrylate, isobutyl acrylate, n-amyl acrylate, isoamyl acrylate, n-ethyl hexyl acrylate, 2-ethyl hexyl acrylate, 2-hydroxy ethyl acrylate, methyl methacrylate, ethyl methacrylate, propyl methacrylate, isopropyl methacrylate, n-butyl methacrylate, isobutyl methacrylate, n-amyl methacrylate, isoamyl methacrylate, n-hexyl methacrylate, n-ethyl hexyl methacrylate, 2-ethyl hexyl methacrylate, hydroxyethyl methacrylate, or hydroxypropyl methacrylate.

The polymerization can be conducted in an organic solvent, water, or a mixture thereof. The organic solvent can be ethyl acetate, toluene, N-methyl-2-pyrollidinone, propylene carbonate, ethylene carbonate, butylene carbonate, dimethyl carbonate, diethyl carbonate, 1,2-dimethoxy ethane, 2-methyl tetrahydrofuran, dimethylsulfoxide, 1,3-dioxolane, formamide, dimethylformamide, dioxolane, acetonitrile, nitromethane, methyl formate, methyl acetate, phosphoric acid triester, trimethoxy methane, methyl sulfolane, 1,3-dimethyl-2-imidazolidinone, methyl propionate, or ethyl propionate.

The polymerization can be conducted in the presence of an initiator. The initiator can be an organic peroxide initiator or an azo initiator. The organic peroxide initiator includes peroxy ketals, dialkyl peroxides, diacyl peroxides, peroxy dicarbonate, peroxide esters, ketone peroxide, hydrogen peroxide. More specifically, the initiator includes 2,2-bis(tert-butyl peroxy)butane, 2,2-bis(tert-butyl peroxy)octane, tert-butyl peroxide, tert-butyl cumyl peroxide, dicumyl peroxide, .alpha.,.alpha.-bis(tert-butyl peroxy isopropyl)benzene, acetyl peroxide, isobutyryl peroxide, lauroyl peroxide, benzoyl peroxide, benzoyl peroxide, diisopropyl peroxy dicarbonate, peracetic acid tert-butyl ester, tert-Butyl peroxyisobutyrate, acetyl acetone peroxide, methyl ethyl ketone peroxide, cyclohexanone peroxide, tert-butyl hydrogen peroxide, cumene hydroperoxide, bis(1-methylethyl) phenyl-hydroperoxide, 2,2-azobisisobutyronitrile, 2,2-azo (2-methyl-butyronitrile) and 1,1-azo(1-cyclohexane carbonitrile).

The polymerization can be conducted at 80-110° C., preferably, at 90-100° C., for 1-4 hours.

A felt, which is made from fibers or other suitable materials, can be added to the polymerization to form a felt-based resin. The felt can be polyester fiber, polypropylene fiber, acrylic fiber, polyacrylonitrile fiber, sponge, aramid fiber, or non-woven fabrics. When the polymerization is conducted in a mixture of an organic solvent and water, the felt is floating on the water and immersed in the monomer, and the monomer is polymerized on the felt to form a felt-based resin. Not bound by any particular theory, it is believed that the resin is attached to the felt via a non-covalent binding interaction, e.g., hydrogen bonding and Van der Waals interactions. The felt has hydrophilic and porous surface, and this surface is maintained in the felt-based resin. The felt can also have fibers with a network structure, and the resin can be evenly distributed on the surface and interspace of the felt fibers. Thus, the microorganisms can be easily immobilized on the felt-based resin, more specifically, on the surface and interspace of the felt fibers. Not bound by any particular theory, it is believed that the microorganisms are immobilized onto the surface and interspace of the felt fibers via a thin biological membrane formed by the internal secretory products of microorganisms. The resin and microorganisms can be alternately distributed on the surface and the interspace of the felt fibers. In contrast, resin beads prepared via a traditional suspension polymerization method has smooth surface, and thus it is difficult to immobilize microorganisms.

Microorganisms immobilized on the felt-based resin can be bacteria. The bacteria include *Pseudomonas putida, Candida albicans, Rhodococcus*, and *Trichosporon*. Preferably, the microorganisms are *Pseudomonas putida*.

Before immobilization, the microorganisms can be treated in an acclimatization process. In the acclimatization process, the microorganisms are treated in a simple minimal salts medium (MSM). The acclimatization process can be carried out by gradually increasing a phenol concentration and gradually decreasing a glucose (carbon source of the microorganisms) concentration in MSM. For example, the microorganisms can be placed an MSM containing 1000 mg/L glucose, and the glucose concentration decreases from 1000 mg/L to 0 at a rate of 100 mg/L per day. At the same time, the phenol concentration in the MSM increases from 0 to 2000 mg/L at a rate of 100 mg/L per day. The original glucose concentration, increasing and decreasing rate, and the final phenol concentration can vary depending the microorganisms. The original glucose concentration can be, for example, 500 mg/L, 750 mg/L, 1000 mg/L, 1250 mg/L, or 1500 mg/L. The increasing and decreasing rate can be, for example, 50 mg/L per day, 75 mg/L per day, 100 mg/L per day, 125 mg/L per day, or 150 mg/L per day. The final phenol concentration can be, for example, 1000 mg/L, 1500 mg/L, 2000 mg/L, 2500 mg/L, 3000 mg/L, 3500 mg/L, 4000 mg/L, 4500 mg/L, or 5000 mg/L. After being treated in an acclimatization process, the microorganisms can use phenol as sole carbon source.

In the immobilization, a container is first charged with the felt-based resin and a liquid culture medium, and microorganisms are added to the mixture of the felt-based resin and medium. By subsequent culturing, the microorganisms are immobilized onto the felt-based resin. The loading amount of the microorganisms can be estimated by measuring the difference of the dry cell weight (DCW) of the microorganisms before and after the immobilization. The thus prepared microorganisms-immobilized felt-based resin can be used to treat phenol-containing effluent at high concentrations (3000-5000 mg/L).

When the microorganisms-immobilized felt-based resin is placed in a high concentration (3000-5000 mg/L) phenol-containing effluent, most of the phenol in the effluent is adsorbed onto the resin rapidly and the phenol concentration is reduced under 2000 mg/L, which is beneficial to the biodegradation of the phenol by the microorganisms. Along with the biodegradation process, the phenol concentration decreases continually and a part of the phenol molecules adsorbed onto the resin ware released back into the effluent due to the concentration driving force. As a result, the microorganisms-immobilized felt-based resin can clean the phenol solution at an initial high concentration of 5000 mg/L and be reused without any extra regeneration process.

REPRESENTATIVE EXAMPLES

Materials n-Butyl acrylate (n-BA), benzoyl peroxide (BPO), ethylene glycol dimethacrylate (EDMA), phenol, inorganic salts and analytical reagent grade were commercially obtained from Sinopharm Chemical Reagent Co., Ltd and used as received without further treatment. Double-distilled water was filtered through a Millipore membrane filter before use. The felt (polyester fiber, 505 g/m$^2$ in weight and 2 cm in thick) was purchased from Shanghai Yanpai Filter-cloth Co., Ltd. A pure strain of *Pseudomonas putida* CICC 21906 was purchased from China Center of Industrial Culture Collection. Tryptone and Yeast extract were purchased from Suzhou Biogene Biotechnology Co., Ltd.

Microbial Culture and Acclimatization

Luria Bertani (LB) liquid medium (compositions listed in Table 1), simple minimal salts medium (MSM) solution (compositions listed in Table 2) and all the apparatus were autoclaved at 121° C. for 15 min, and glucose and phenol were separately sterilized by membrane filter (0.22 μm). After amplifying in LB liquid medium with the constituents shown in Table 1, the *Pseudomonas putida* was placed in 50 mL of MSM solution containing 1000 mg/L of glucose (a commonly used organic carbon source) and incubated at 30° C., 200 rpm for 24 h. The acclimatization process was carried out by gradual increase in the phenol concentration (100 mg/L per day) in combination with a gradual reduction in the glucose concentration (100 mg/L per day) in MSM until the glucose was utterly replaced by phenol as sole carbon source. And then, the phenol concentration was further increased to 2000 mg/L with the rate of 100 mg/L per day in order to keep the efficient biodegradation of the bacteria.

TABLE 1

Compositions of LB liquid medium

| Component | Concentration (g/l) |
| --- | --- |
| Tryptone | 10 |
| Yeast extract | 5 |
| NaCI | 10 |
| NaOH | Adjust pH to 7.4 |

TABLE 2

Compositions of nutrient mineral salt medium (MSM)

| Component | Concentration (mg/l) |
| --- | --- |
| $MgSO_4 \cdot 7H_2O$ | 300 |
| $K_2HPO_4$ | 250 |
| $CaCl_2 \cdot 2H_2O$ | 150 |
| $NH_4Cl$ | 130 |
| $FeSO_4 \cdot 7H_2O$ | 3.5 |
| $ZnSO_4 \cdot 7H_2O$ | 1.3 |
| $MnCl_2 \cdot 4H_2O$ | 0.13 |
| NaCl | 0.02 |
| $CuSO_4 \cdot 5H_2O$ | 0.018 |
| $CoCl_2 \cdot 6H_2O$ | 0.015 |

Biodegradation of Phenol by Free Bacterial Cells

In order to investigate the biodegradation performance of phenol for free bacterial cells at different pH (2-12) and temperatures (25-45° C.), batch experiments were carried out in 250 mL erlenmeyer flasks keeping a constant phenol concentration of 1000 mg/L (as a representative) in 50 mL MSM and shaking at 30° C., 120 rpm for 1 d, respectively. And then, the biodegradation efficiency and the optical density at the wavelength of 600 nm ($OD_{600}$) of the bacterial system were measured at the optimum conditions. $OD_{600}$ represents the real-time bacterial cell density, which is dependent on the growth of bacteria in the corresponding time.

Synthesis of the Felt-based BA-resin

The new felt-based BA-resin was obtained after the cross-linked polymerization of butyl acrylates monomers on felt. Firstly, 2.0 g BPO and 1.0 g EDMA were dissolved in the mixture of 200 mL BA and 200 mL methylbenzene in an enamel vessel. And then, a piece of the polyster felt (300× 200 mm$^2$, 20 mm-thick) was dipped into the above organic solution mixed with 800 mL $H_2O$ in order that the monomers could polymerize on the felt with a uniform distribution during the polymerization process in a water bath at 95° C. for 5 h. After washing with ethanol and distilled water, the felt-based BA-resin was dried at room temperature and cut into small pieces (5×5×5 mm$^3$) for later use.

Immobilization of Bacteria Onto the Felt-based BA-resin

Before the immobilization, all utensils and the carriers were autoclaved at 121° C. for 15 min. The immobilization process was carried out in a 250 mL erlenmeyer flask, and 50 mL MSM suspension of acclimatized *Pseudomonas putida* (containing 1000 mg/L of phenol) was incubated at 30° C. And then, 7.0 g of felt-based BA-resin was added in the suspension and kept shaking in the constant temperature oscillator at 30° C. for 24 h. The loading amount of *Pseudomonas putida* cells was estimated by determining the difference of the dry cell weight (DCW) before and after immobilization.

Acclimatization of *Pseudomonas putida* and Effect of Temperature and pH

*Pseudomonas putida* was activated and amplified with LB liquid medium. And then, the bacteria were transferred to the MSM mentioned above. Acclimatization of the bacteria during the adaptation process was presented in FIG. 1. In the first stage, the *Pseudomonas putida* could not use phenol as the sole carbon source for its inhibition to the bacteria. Increasing the phenol concentration as well as decreasing the glucose concentration at the same rate of 100 mg/L per day, the *Pseudomonas putida* began to adapt to phenol gradually. After the acclimatization for several days, the *Pseudomonas putida* could degrade phenol completely in the absence of glucose, which indicated that the *Pseudomonas putida* was activated by phenol as the sole carbon source and energy source. When the phenol concentration was further increased up to 2000 mg/L (also 100 mg/L per day), the free cells system maintained at favorable degradation efficiency. But it began to decay after increasing the phenol concentration beyond 2000 mg/L. That was to say, the free cells system of *Pseudomonas putida* could be acclimatized to degrade phenol at the concentration below 2000 mg/L.

3.2 Biodegradation of Phenol by Free Cells System

The biodegradation rate of phenol for free cells was investigated as shown in FIG. 2. It was obvious that phenol could be biodegraded completely by the *Pseudomonas putida* within 16 h at the initial phenol concentration of 1000 mg/L and the reduction of phenol concentration was almost linearly versus time as well as the increment of $OD_{600}$. The increasing amount of DCW was calculated to be 8.25 mg against the related conversion curve (FIG. 3).

Adsorption of Phenol by Felt-based BA-resin

The adsorption of phenol by each component of the felt-based BA-resin was investigated respectively in the same experimental conditions, and the results were shown in FIG. 4. It was obvious that the BA-resin beads without felt substrate achieved a favorable removal rate of phenol about 80% within 1 h. But because of the smooth spherical surface, they are not suitable for the immobilization of bacteria. In order to solve this problem, a non-toxic commercial felt had been selected to be the matrix of cross-linked BA-resin and bacteria. Although the felt itself had little adsorption performance of phenol, but for its reticular structure, it was suitable for the immobilization of bacteria. Therefore, the felt-based BA-resin had been prepared to meet the requirements.

The new felt-based BA-resin was prepared by a new method based on solution polymerization and the average weight of the felt-based BA-resin was 2729.41 g/m² (20 mm-thick) and the average content of BA-resin was 83.59% in weight. Compared with that of the BA-resin beads without felt substrate, the removal rate of phenol by felt-based BA-resin around 75% is a little bit lower, but it is much higher than other common matrix for cell immobilization such as polyurethane, pumice and polyvinyl alcohol (PVA) gel.

Equilibrium adsorption experiments were carried out at 303 K and then a series of 50 mL solutions at different phenol concentrations ranged from 1000 to 5000 mg/L were added into the 250 mL flasks. After shaking for about 4 h, the adsorption process attained equilibrium.

It was obvious that most of phenol could be adsorbed within 1 h (FIG. 5) and the removal rates of phenol at equilibrium state kept around 75% at different initial concentrations. According to the adsorption equilibrium data (FIG. 5), the value of $Q_e$ (the adsorption amount of phenol) was found to be linearly increased with the increasing of $C_e$ (the equilibrium concentration) at 303 K. That was to say, the initial phenol concentration had little effect on the adsorption performance of felt-based BA-resin and it could be used directly at high phenol concentration (5000 mg/L) to meet the industrial requirements.

In order to further evaluate the adsorption of phenol by felt-based BA-resin, the most frequently employed models, Langmuir and Freundlich isotherm models were used to describe the relationship between the adsorption amount of phenol and its equilibrium concentration in solution at different temperature.

The Langmuir isotherm model is based on the supposition that the adsorption process is happened at the monolayer of the surface and there is no interaction between the solute molecules adsorbed on the surface and free in the solution. The linear form of the Langmuir isotherm model can be written as:

$$C_e/q_e = C_e/Q_m + 1/(K_L \cdot Q_m) \quad (7)$$

Where $q_e$ is the adsorption amount of phenol at equilibrium (mg/g), $Q_m$ is the theoretical monolayer capacity (mg/g), $C_e$ is the residual phenol concentration at equilibrium (mg/L) and $K_L$ is the constant.

The Freundlich isotherm supposes that the adsorption take place at heterogeneous surface. The logarithmic linear form of the Freundlich isotherm model is given as:

$$lnQ_e = lnK_F + (1/n)lnC_e \quad (8)$$

Where $K_F$ is the Freundlich isotherm constant (L/g) reflecting the adsorption capacity and 1/n is the value of adsorption intensity.

The values of isotherm constants and correlation coefficient ($R^2$) are listed in Table 3. The $R^2$ values in both isotherm models were greater than 0.988. That was to say, the equilibrium data fit both Freundlich isotherm and Langmuir isotherm models well, which indicated that the adsorption process contained both monolayer adsorption and heterogeneous surface adsorption.

TABLE 3

Isotherm parameters for phenol adsorption by felt-based BA-resin

| | Freundlich model $lnQ_e = lnK_F + (1/n)lnC_e$ | | | Langmuir model $C_e/Q_e = C_e/Q_m + 1/(K_L Q_m)$ | | |
|---|---|---|---|---|---|---|
| T/K | $K_f$ | n | $R^2$ | $Q_m$ | $K_L$ | $R^2$ |
| 303K | 0.019726 | 1.03213 | 0.9999 | 392.1569 | 0.000042 | 0.9880 |

In detail, the adsorption of phenol by felt-based BA-resin could be divided into two stages: an initial rapid stage and a subsequent slow stage. At the beginning of the experiment, the adsorption rate of phenol was very fast because there were many vacant adsorption sites on the surface of BA-resin (generated by the hydrogen bonding interaction between phenol and BA-resin) for phenol molecules to fill up. And then, with the monolayer adsorption reaching saturation state gradually, the adsorption rate became slow. It was because the hydrogen bonding interaction from the heterogeneous surface adsorption was much weaker than that from the monolayer adsorption. In addition, the existence of water molecules also weakened the hydrogen bonding interaction of the heterogeneous surface adsorption.

So it took a relatively long time to reach the equilibrium state in the whole adsorption process.

In order to understand the whole adsorption process of phenol by felt-based BA-resin, the release experiments were carried out in the same conditions (FIG. 6). After the adsorption of phenol attained equilibrium, the felt-based BA-resin was moved into distilled water. Since the hydrogen bonding interactions between the resin surface and phenol molecules were weakened by the competition of more water molecules, a part of phenol molecules adsorbed on the resin were released in water gradually until a new equilibrium state was achieved. As shown in FIG. 6, the phenol concentration at final equilibrium state is kept not exceeding 1000 mg/L even though the initial concentration is 5000 mg/L. It is significant and beneficial for bacteria to be combined with.

Immobilization of *Pseudomonas putida* Onto the Felt-based BA-resin

After the synthetic process, the BA-resin was evenly distributed evenly on the surface and the interspaces of the felt fibers (FIG. 7b). And then, the cells of *Pseudomonas putida* were immobilized on the felt-based BA-resin by adhering to the felt fiber during the immobilization process and a thin biological membrane was formed on the surface of the felt-based BA-resin (FIG. 7c). The cells of *Pseudomonas putida* could be clearly observed under the microscope after being stained with Giemsa colorant (FIGS. 7d and 7e) and the loading amount of bacteria converted to DCW was 29.64 mg/g. The 3D schematic diagram (FIG. 7f) could simulate the preparation process of the microbe-resin composite material based on the felt. It was worth mentioning that the bacterial cells were fixed in the felt meshes of the reticular fibers, rather than to adhere to the hydrophobic and smooth surface of BA-resin. Therefore the colonies of bacterial cells and BA-resin were alternately distributed on the felt, which was advantageous to the mass transfer and the diffusion of phenol in this system.

The Adsorption-biodegradation Process of Cells-immobilized Felt-based BA-resin

The adsorption-biodegradation experiments were carried out in the flasks containing 7.0 g of cells-immobilized felt-based BA-resin at different initial phenol concentrations ranged from 3000-5000 mg/L and the results were shown in FIG. 8. According to the adsorption of phenol by cells-free felt-based BA-resin discussed above, the adsorption-biodegradation process of cells-immobilized felt-based BA-resin also could be divided into two stages (signed by the red dotted line in FIG. 8). The initial rapid stage with sharply decrease of phenol concentration is similar to that of felt-based BA-resin because the adsorption effect of the felt-based BA-resin played a main role in this short stage (with 1 h) and the phenol concentration was decreased to a low level (<2000 mg/L) which could avoid the damage to the bacterial cells. Then in the second stage, the cells started degradation as soon as the phenol concentration decreased below the limitation of the biodegradation by bacteria until a clean removal of phenol was achieved. The dynamic adsorption-release balance and the biodegradation of *Pseudomonas putida* worked together to complete the biodegradation process. So it was different from the simple adsorption process of the felt-based BA-resin that maintained at an equilibrium concentration.

It took several hours to completely biodegrade the phenol not for the decreasing of the biodegradation efficiency of *Pseudomonas putida* but owning to the adsorption-release balance of phenol by the felt-based BA-resin following with the biodegradation process all the time. During the biodegradation process, the phenol concentration decreased in the solution and the adsorption equilibrium was broken which lead parts of phenol molecules adsorbed on the felt-based BA-resin to release into the solution. Under the synergy of adsorption-release-biodegradation process, thick phenol solutions could be completely degraded within 60, 70 and 80 h from the initial concentration of 3000, 4000 and 5000 mg/L, respectively. It should be mentioned that the regeneration of felt-based BA-resin was performed as well as the biodegradation of phenol was finished. So it can be recycled for next treatment of phenol without any special regeneration process.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method of preparing a microorganisms-immobilized felt-based resin comprising:
   providing a mixture consisting of an acrylate monomer, an initiator, an organic solvent, a felt, and water,
   initiating a polymerization reaction of the mixture consisting of the acrylate monomer, the initiator, the organic solvent, the felt, and water to form a felt-based resin, and
   immobilizing microorganisms on the felt-based resin to form the microorganisms-immobilized felt-based resin,
   wherein the acrylate monomer is polymerized on the felt with a uniform distribution to form the felt-based resin in the mixture consisting of the acrylate monomer, the initiator, the organic solvent, the felt, and water;
   wherein the organic solvent is selected from the group consisting of ethyl acetate, toluene, N-methyl-2-pyrolidinone, propylene carbonate, ethylene carbonate, butylene carbonate, dimethyl carbonate, diethyl carbonate, 1,2-dimethoxy ethane, 2-methyl tetrahydrofuran, dimethylsulfoxide, 1,3-dioxolane, formamide, dimethylformamide, dioxolane, acetonitrile, nitromethane, methyl formate, methyl acetate, phosphoric acid triester, trimethoxy methane, methyl sulfolane, 1,3-dimethyl-2-imidazolidinone, methyl propionate, and ethyl propionate;
   wherein the acrylate monomer is selected from the group consisting of methyl acrylate, ethyl acrylate, propyl acrylate, isopropyl acrylate, n-butyl acrylate, isobutyl acrylate, n-amyl acrylate, isoamyl acrylate, n-ethyl hexyl acrylate, 2-ethyl hexyl acrylate, 2-hydroxy ethyl acrylate, methyl methacrylate, ethyl methacrylate, propyl methacrylate, isopropyl methacrylate, n-butyl methacrylate, isobutyl methacrylate, n-amyl methacrylate, isoamyl methacrylate, n-hexyl methacrylate, n-ethyl hexyl methacrylate, 2-ethyl hexyl methacrylate, hydroxyethyl methacrylate, and hydroxypropyl methacrylate;
   wherein the initiator is an organic peroxide initiator or an azo initiator; and
   wherein the felt includes fibers with a network structure, and the microorganisms are distributed on the surface and interspace of the fibers.

2. The method of claim 1, wherein the microorganisms are selected from the group consisting of *Pseudomonas putida, Candida albicans, Rhodococcus*, and *Trichosporon*.

3. The method of claim 1, wherein the initiator is in an amount of 0.01 wt % to 5 wt % based on the weight of the acrylate monomer, the organic solvent is in an amount of 100 wt % to 200 wt % based on the weight of the acrylate monomer, and water is in an amount of 100 wt % to 500 wt % based on the weight of the acrylate monomer.

4. The method of claim 1, the felt is selected from the group consisting of polypropylene fiber, acrylic fiber, polyacrylonitrile fiber, sponge, aramid fiber, and non-woven fabrics.

5. The method of claim 1, wherein the microorganisms are treated in an acclimatization process before immobilization.

6. The method of claim 5, wherein the acclimatization process comprising gradually increasing a phenol concentration and gradually decreasing a glucose concentration.

7. The method of claim 6, wherein the phenol concentration increases from 0 to 2000 mg/L at a rate of 100 mg/L per day.

8. The method of claim 6, wherein the glucose concentration decreases from 1000 mg/L at a rate of 100 mg/L per day.

9. A microorganisms-immobilized felt-based resin prepared by the following steps:
   providing a mixture consisting of an acrylate monomer, an initiator, an organic solvent, a felt and water,
   initiating a polymerization reaction of the mixture consisting of the acrylate monomer, the initiator, the organic solvent, the felt, and water to form a felt-based resin, and
   immobilizing microorganisms on the felt-based resin to form the microorganisms-immobilized felt-based resin,
   wherein the acrylate monomer is polymerized on the felt with a uniform distribution to form the felt-based resin in the mixture consisting of the acrylate monomer, the initiator, the organic solvent, the felt, and water;
   wherein the organic solvent is selected from the group consisting of ethyl acetate, toluene, N-methyl-2-pyrrolidinone, propylene carbonate, ethylene carbonate, butylene carbonate, dimethyl carbonate, diethyl carbonate, 1,2-dimethoxy ethane, 2-methyl tetrahydrofuran, dimethylsulfoxide, 1,3-dioxolane, formamide, dimethylformamide, dioxolane, acetonitrile, nitromethane, methyl formate, methyl acetate, phosphoric acid triester, trimethoxy methane, methyl sulfolane, 1,3-dimethyl-2-imidazolidinone, methyl propionate, and ethyl propionate;
   wherein the initiator is an organic peroxide initiator or an azo initiator;
   wherein the acrylate monomer is selected from the group consisting of methyl acrylate, ethyl acrylate, propyl acrylate, isopropyl acrylate, n-butyl acrylate, isobutyl acrylate, n-amyl acrylate, isoamyl acrylate, n-ethyl hexyl acrylate, 2-ethyl hexyl acrylate, 2-hydroxy ethyl acrylate, methyl methacrylate, ethyl methacrylate, propyl methacrylate, isopropyl methacrylate, n-butyl methacrylate, isobutyl methacrylate, n-amyl methacrylate, isoamyl methacrylate, n-hexyl methacrylate, n-ethyl hexyl methacrylate, 2-ethyl hexyl methacrylate, hydroxyethyl methacrylate, and hydroxypropyl methacrylate; and
   wherein the felt includes fibers with a network structure, and the microorganisms are distributed on the surface and interspace of the fibers.

10. A method of cleaning a phenolic effluent comprising:
    preparing a microorganisms-immobilized felt-based resin prepared in accordance with the method of claim 1, and
    treating the phenolic effluent with the microorganisms-immobilized felt-based resin.

11. The method of claim 10, wherein the phenolic effluent has a phenol concentration of 1000-5000 mg/L.

* * * * *